United States Patent [19]
Fisher et al.

[11] Patent Number: 5,869,425
[45] Date of Patent: Feb. 9, 1999

[54] VARIOUS SYNERGISTIC HERBICIDAL COMPOSITIONS

[75] Inventors: James Delbert Fisher, Lansdale; Colin Michael Tice, Elkins Park, both of Pa.

[73] Assignee: Rohm and Haas Company, Philadelphia, Pa.

[21] Appl. No.: 858,427

[22] Filed: May 19, 1997

Related U.S. Application Data

[60] Provisional application No. 60/018,161, May 23, 1996.
[51] Int. Cl.$^6$ .......................... A01N 33/00; A01N 37/18; A01N 47/10
[52] U.S. Cl. ........................ 504/143; 504/148; 504/149
[58] Field of Search .................................. 504/143, 148, 504/149

[56] References Cited

U.S. PATENT DOCUMENTS 5,212,193  5/1993  Sherba et al. ............................ 514/372

FOREIGN PATENT DOCUMENTS 42 09 475 A1  9/1993  Germany .
42 41 629 A1  6/1994  Germany .

OTHER PUBLICATIONS

Tomlin, The Pesticide Manual, pp. 49, 50, 845 & 846 10th Ed (1995).
Smith, Weed Res. (1984) Abst. only.

*Primary Examiner*—Allen J. Robinson
*Attorney, Agent, or Firm*—Clark R. Carpenter

[57] ABSTRACT

The present invention relates to compositions, having herbicidal synergistic effects, comprising
  (i) propanil;
  (ii) a compound selected from asulam, butamifos and methazole; and
  (iii) an agronomically acceptable carrier
for the control of various grasses and broadleaf weeds in rice. More particularly, such compositions exhibit synergistic properties for selectively controlling weeds in rice, especially grassy weeds such is Barnyardgrass, Junglerice, Signalgrass and Sprangletop. This invention also relates to a method of controlling weed species in rice comprising applying a herbicidally effective amount of composition comprising (i) propanil, (ii) a compound selected from asulam, butamifos and methazole and (iii) an agronomically acceptable carrier to the weed, to the locus of the weed or to the growth medium of said weed.

4 Claims, No Drawings

VARIOUS SYNERGISTIC HERBICIDAL COMPOSITIONS

This application claims the benefit of the filing date of U.S. provisional application Ser. No. 60/018,161 filed May 23, 1996.

The present invention relates to compositions having herbicidal synergistic effects. In particular, the present invention relates to the use of compositions comprising propanil, a compound selected from asulam, butamifos and methazole, and an agronomically acceptable carrier as selective postemergence compositions for the control of various grasses and broadleaf weeds in rice. More particularly, such compositions exhibit synergistic properties for selectively controlling weeds in rice, especially grassy weeds such as Barnyardgrass, Junglerice, Signalgrass and Sprangletop. Such compositions are especially noteworthy for control of Junglerice, some biotypes of which show resistance to conventional herbicide treatments.

Typical compositions containing chemical weed control agents enable more efficient crop production by minimization of competing plant growth. New chemical means of controlling such unwanted vegetation are desirable in order to obtain better control of various agronomically important weeds, for better crop safety and to overcome herbicide resistance. Although many herbicides, including propanil, asulam, butamifos and methazole, are well known individually as chemical weed control agents for rice crops, their control is not sufficient at normal dosage rates to control certain grassy weeds effectively. The resulting competition from such weeds attenuates the yield of rice from the plantings with its attendant economic disadvantage. If the dosage rates of propanil, asulam, butamifos or methazole are increased to the extent necessary to effectively control the weed species, selectivity to the rice crop itself is diminished. This again attenuates the yield of rice. A need therefore exists for a more economical and a more selective method for controlling such weed species in rice crops.

It has been unexpectedly found that compositions comprising propanil and a compound selected from asulam, butamifos and methazole result in enhanced control of weed species in rice, especially grassy weed species, without an increase in dosage rate and its attendant selectivity problems to the rice crop. The herbicidal compositions may be applied to the rice crop or to the locus where the rice crop is to be grown either before the emergence of the undesired weed vegetation or, more preferably, after the emergence of the undesired weed vegetation.

The herbicidal compositions of this invention comprise
(i) propanil;
(ii) a compound selected from asulam, butamifos and methazole; and
(iii) an agronomically acceptable carrier.

As used to describe the present invention, propanil is the common name for N-(3,4-dichlorophenyl)propanamide, asulam is the common name for methyl 4-aminobenzenesulfonylcarbamate, butamifos is the common name for O-ethyl-O-(3-methyl-6-nitrophenyl)-N-sec-butylphosphorothioamidate, and methazole is the common name for 2-(3,4-dichlorophenyl)-4-methyl-1,2,4-oxadiazolidine-3,5-dione.

A second embodiment of this invention relates to a method of controlling weed species in rice comprising applying a herbicidally effective amount of a composition comprising (i) propanil, (ii) a compound selected from asulam, butamifos and methazole, and (iii) an agronomically acceptable carrier to the weed, to the locus of the weed or to the growth medium of said weed. The relative proportion of the amount of propanil to asulam, butamifos or methazole to be used for enhanced control of weed species in rice varies from about 32 to about 1 part by weight of propanil to about one part by weight of asulam, butamifos or methazole. Preferably, the proportion is from about 16 to about 3 parts by weight of propanil to about one part by weight of asulam, butamifos or methazole.

The compositions of this invention are useful in both preemergence and postemergence applications, particularly in postemergence applications. Preemergence compositions are usually applied to the soil either before, during or after seeding, but before the crop emerges. Postemergence herbicides are applied after the plants have emerged and during their growth period, The embodied compositions show selectivity to rice while exhibiting good control of Barnyardgrass, Junglerice, Signalgrass and Sprangletop.

Under some conditions the compositions of the invention may be incorporated into the soil or other growth medium prior to planting a crop. This incorporation may be by any convenient means, including mixing with the soil, applying the compound to the surface of the soil and then discing or dragging into the soil lo the desired depth, or by employing a liquid carrier.

The compositions of the present invention can be applied to various loci such as the soil or the foliage. The compositions are usually taken up in a carrier or are formulated so as to render them suitable for subsequent dissemination as a herbicidal composition. For example, these chemical agents can be formulated as wettable powders, emulsifiable concentrates, dusts, granular formulations, aerosols, or flowable emulsion concentrates. In such formulations, the compositions are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual." Allured Publishing Company, Ridgewood, N.J., U.S.A.

The compositions of this invention can be applied as herbicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and weeds to be controlled, but the preferred effective amount is usually at about 1.2 kg. per hectare of the active ingredient propanil and from about 0.3 kg. per hectare to about 0.02 kg. per hectare of the active ingredient asulam, butamifos or methazole.

The compositions of this invention can also be mixed with fertilizers or fertilizing materials before their application. In one type of solid fertilizing composition in which the compositions of this invention can be used, particles of a fertilizer or fertilizing ingredients, such as ammonium sulfate, ammonium nitrate, or ammonium phosphate, can be coated with a composition of this invention. The solid compounds and solid fertilizing material can also be admixed in mixing or blending equipment, or they can be incorporated with fertilizers in granular formulations. Any relative proportion of fertilizer can be used which is suitable for the crops and weeds to be treated. These compositions provide fertilizing materials which promote the rapid growth of desired plants, and at the same time control the growth of undesired plants.

The herbicidal activity of the compositions of the present invention towards a number of common weeds was evaluated using a greenhouse method of testing. Using the greenhouse test methods described below, propanil, asulam, butamifos and methazole, and the compositions of the present invention comprising propanil and asulam, butamifos or methazole were evaluated for control of weeds in rice selected from the following:

| Common Name | Code | Scientific name |
|---|---|---|
| Barnyardgrass | (BYG) | *Echinochloa crus-galli* |
| Junglerice | (JUN) | *Echinochloa colonum* |
| Sprangletop | (SPR) | *Leptochloa dubia.* |

Seeds of selected plants were planted in flats or pots. For preemergence tests, immediately after planting, the test compound was sprayed directly onto the soil surface. The flats or pots were placed in the greenhouse and then watered. For postemergence tests, the seeds were allowed to germinate and grow for 10 to 21 days. Before application, each series of test plants was selected for uniformity, size and stage of development. The test plants were then treated with the test compound, returned to the greenhouse and watered.

The compound or composition to be evaluated was dissolved in an appropriate solvent, usually acetone, and sprayed over the flats or pots using a carrier volume equivalent to 234 or 268 liters per hectare at the rate of application in grams per hectare (g/Ha) specified in Tables I. About two or three weeks after application of the test compound, the stage of growth of the plant was observed. Each species was evaluated on a scale of 0–100 in which 0 equals no activity and 100 equals total control.

TABLE I

GREENHOUSE POSTEMERGENCE DATA

| Compound or Composition | Rate in g/Ha | Rice | BYG | JUN | SPR |
|---|---|---|---|---|---|
| propanil (only) | 4800 | 0 | 60 | 0 | 0 |
| propanil (only) | 3600 | 0 | 100 | 0 | 50 |
| propanil (only) | 3600 | 0 | 100 | 0 | 100 |
| asulam (only) | 300 | 0 | 0 | 15 | 0 |
| butamifos (only) | 1200 | 0 | 75 | 0 | 30 |
| methazole (only) | 300 | 0 | 100 | 70 | 0 |
| propanil + asulam | 4800 + 300 | 15 | 95 | 60 | 75 |
| propanil + butamifos | 3600 + 1200 | 0 | 100 | 73 | 100 |
| propanil + methazole | 3600 + 300 | 20 | 100 | 100 | 100 |

It is to be understood that changes and variations may be made without departing from the spirit and scope of the invention as defined by the appended claims.

We claim:

1. A synergistic herbicidal composition comprising (i) about 16 parts by weight of propanil;

(ii) 1 part by weight of asulam; and (iii) an agronomically acceptable carrier.

2. A method of controlling weed species in rice comprising applying an effective amount of a synergistic herbicidal composition comprising (i) about 16 parts by weight of propanil;

(ii) 1 part by weight of asulam; and (iii) an agronomically acceptable carrier to the weed, to the locus of the weed or to the growth medium of said weed such that about 1.2 kg. per hectare of propanil and about 0.075 kg. per hectare of asulam is applied.

3. The method of claim 2 for controlling weed species in rice wherein the weeds controlled are Barnyardgrass, Junglerice, Signalgrass and Sprangletop.

4. The method of claim 3 wherein the weeds controlled are Barnyardgrass, Junglerice and Sprangletop.

* * * * *